(12) United States Patent
Li et al.

(10) Patent No.: US 10,946,009 B2
(45) Date of Patent: Mar. 16, 2021

(54) COMBINATION DOSAGE FORM OF A MU OPIOID RECEPTOR ANTAGONIST AND AN OPIOID AGENT

(71) Applicant: THERAVANCE BIOPHARMA R&D IP, LLC, South San Francisco, CA (US)

(72) Inventors: Shaoling Li, Sunnyvale, CA (US); Manshiu Leung, Daly City, CA (US); Hao Zhang, Foster City, CA (US); Venkat R. Thalladi, Foster City, CA (US); Yun Mo, Foster City, CA (US)

(73) Assignee: Theravance Biopharma R&D IP, LLC, South San Francisco, CA (US)

( * ) Notice: Subject to any disclaimer, the term of this patent is extended or adjusted under 35 U.S.C. 154(b) by 74 days.

(21) Appl. No.: 16/454,353

(22) Filed: Jun. 27, 2019

(65) Prior Publication Data

US 2019/0321350 A1   Oct. 24, 2019

Related U.S. Application Data

(62) Division of application No. 15/798,647, filed on Oct. 31, 2017, now Pat. No. 10,369,142, which is a division of application No. 15/086,816, filed on Mar. 31, 2016, now abandoned.

(60) Provisional application No. 62/141,981, filed on Apr. 2, 2015.

(51) Int. Cl.
| | |
|---|---|
| *A61K 31/46* | (2006.01) |
| *A61K 31/439* | (2006.01) |
| *A61K 9/24* | (2006.01) |
| *A61K 31/485* | (2006.01) |
| *A61K 9/28* | (2006.01) |

(52) U.S. Cl.
CPC .............. *A61K 31/46* (2013.01); *A61K 9/209* (2013.01); *A61K 9/282* (2013.01); *A61K 9/284* (2013.01); *A61K 9/2853* (2013.01); *A61K 9/2893* (2013.01); *A61K 31/439* (2013.01); *A61K 31/485* (2013.01)

(58) Field of Classification Search
CPC ...... A61K 31/46; A61K 31/439; A61K 9/209; A61K 9/2893; A61K 9/282; A61K 9/2853; A61K 9/284
See application file for complete search history.

(56) References Cited

U.S. PATENT DOCUMENTS

| | | | |
|---|---|---|---|
| 6,277,384 B1 | 8/2001 | Kaiko et al. | |
| 6,451,806 B2 | 9/2002 | Farrar | |
| 7,622,508 B2 | 11/2009 | Long et al. | |
| 7,842,307 B2 | 11/2010 | Oshlack et al. | |
| 7,932,402 B2 | 4/2011 | Colson et al. | |
| 7,943,772 B2 | 5/2011 | Dalziel et al. | |
| 7,951,400 B2 | 5/2011 | Desai et al. | |
| 8,246,986 B2 | 8/2012 | Cruz et al. | |
| 8,247,555 B2 | 8/2012 | Dalziel et al. | |
| 8,247,559 B2 | 8/2012 | Colson et al. | |
| 8,263,618 B2 | 9/2012 | Long et al. | |
| 8,476,440 B2 | 7/2013 | Colson et al. | |
| 8,536,335 B2 | 9/2013 | Dalziel et al. | |
| 8,580,310 B2 | 11/2013 | Krishnamurthy et al. | |
| 8,664,242 B2 | 3/2014 | Long et al. | |
| 8,685,450 B2 | 4/2014 | Lim et al. | |
| 8,816,091 B2 | 8/2014 | Dalziel et al. | |
| 8,927,573 B2 | 1/2015 | Long et al. | |
| 9,206,172 B2 | 12/2015 | Long et al. | |
| 9,290,491 B2 | 3/2016 | Dalziel et al. | |
| 9,663,509 B2 | 5/2017 | Long et al. | |
| 9,949,963 B2 | 4/2018 | Dalziel et al. | |
| 10,081,626 B2 | 9/2018 | Long et al. | |
| 2006/0199839 A1 | 9/2006 | Goldblum et al. | |
| 2007/0219278 A1 | 9/2007 | Long et al. | |
| 2008/0207676 A1 | 8/2008 | Dalziel et al. | |
| 2008/0269198 A1 | 10/2008 | Benjamin et al. | |
| 2010/0291183 A1 | 11/2010 | Farrell et al. | |
| 2011/0287093 A1 | 11/2011 | Schoenhard | |
| 2012/0009227 A1 | 1/2012 | Humar et al. | |
| 2013/0164384 A1 | 6/2013 | Johnson et al. | |
| 2014/0079778 A1 | 3/2014 | Narang et al. | |
| 2014/0271862 A1 | 9/2014 | Jacob et al. | |
| 2018/0050028 A1 | 2/2018 | Li et al. | |
| 2018/0200246 A1 | 7/2018 | Dalziel et al. | |
| 2019/0119267 A1 | 4/2019 | Long et al. | |

FOREIGN PATENT DOCUMENTS

| | | |
|---|---|---|
| CN | 101500542 A | 8/2009 |
| CN | 102858324 A | 1/2013 |
| JP | 2009-185046 A | 8/2009 |
| JP | 2013-538814 A | 10/2013 |

OTHER PUBLICATIONS

Yao, Jing, "Application directory of pharmaceutical excipients", China Medical Science and Technology Press, pp. 37-39 (2011).
Yao, Risheng, "Pharmaceutical polymer materials", Chemical Industry Press, pp. 166-167 (2003).
International Search Report for PCT/US2016/025176 dated Jun. 24, 2016.
Koo et al., "Investigation into Stability of Poly(Vinyl Alcohol)-Based Opadry II Films", AAPS PharmSci Tech, 2011, vol. 12, No. 2, pp. 746-754.
Poster Presentation, Abstract 0520, PAINWeek 2015, Sep. 8-12, 2015, Las Vegas, NV.
Theravance Biopharma, Inc., Investor and Analyst' Day Presentation, New York, NY (Dec. 12, 2014).

*Primary Examiner* — Mina Haghighatian
(74) *Attorney, Agent, or Firm* — Jeffrey A. Hagenah; Florence Jovic

(57) ABSTRACT

The invention provides a solid composition of the peripheral mu opioid antagonist axelopran and a combination dosage form of the mu opioid antagonist axelopran sulfate in an immediate release form and an opioid analgesic agent which may be in an extended release, sustained release, modified release, or controlled release form and methods of preparing such a combination dosage form.

14 Claims, 6 Drawing Sheets

COMBINATION DOSAGE FORM OF A MU OPIOID RECEPTOR ANTAGONIST AND AN OPIOID AGENT

CROSS-REFERENCE TO RELATED APPLICATIONS

This application is a divisional of U.S. Ser. No. 15/798,647, filed on Oct. 31, 2017, now allowed; which is a divisional application of U.S. Ser. No. 15/086,816, filed on Mar. 31, 2016, now abandoned; which application claims the benefit of U.S. Provisional Application No. 62/141,981, filed on Apr. 2, 2015 the disclosure of which is incorporated herein by reference in its entirety.

BACKGROUND OF THE INVENTION

Field of the Invention

The invention is directed to a solid composition of a peripheral mu opioid receptor antagonist and to a combination of the mu opioid receptor antagonist composition and an opioid analgesic agent. In particular, the invention is directed to a unit dosage form in which the mu opioid receptor antagonist is in an immediate release form and the opioid analgesic agent may be in an extended release, sustained release, modified release, or controlled release form and to methods of preparing such a unit dosage form.

State of the Art

Compounds which function as agonists at opioid receptors, of which oxycodone, hydrocodone, morphine, and oxymorphone are common examples, are the mainstays of analgesic therapy for the treatment of moderate to severe pain. It is understood that opioid analgesics exert their beneficial effect chiefly by activation of mu opioid receptors in the brain and central nervous system. However, opioid receptors are expressed throughout the body, both in the central nervous system and in peripheral regions including the gastrointestinal (GI) tract. Unfortunately, adverse side effects of the use of opioid analgesics may be caused by activation of these peripheral receptors. In particular, patients receiving opioids analgesics for short or long term pain management frequently experience a range of adverse gastrointestinal symptoms, in particular opioid induced constipation (OIC). Encompassing constipation, delayed gastric emptying, abdominal discomfort, and nausea, OIC can be extremely debilitating and is not prone to tolerance. Gastrointestinal symptoms may be severe enough to seriously compromise pain management for some patients.

Peripherally acting opioid antagonist compounds that do not readily cross the blood-brain barrier have been shown to be beneficial in counteracting opioid-induced constipation. In particular, axelopran, 3-((1R,3r,5S)-8-(2-((cyclohexylmethyl)((2S)-2,3-dihydroxypropanoyl)amino)ethyl)-8-azabicyclo[3.2.1]octan-3-yl)benzamide,

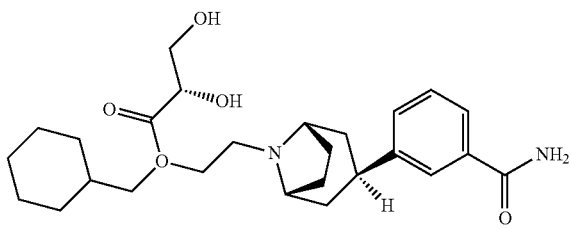

(U.S. Pat. Nos. 7,622,508 and 7,943,772) has been demonstrated clinically to ameliorate the symptoms of OIC in non-cancer pain patients on a stable opioid regimen without compromising analgesia. (Vickery et al. Pain Week 2012, Las Vegas, Nev. (P-87).

Patients taking opioid analgesics for pain management may find it useful to also take a peripheral opioid antagonist to manage adverse side effects of their pain medication. Such patients, who may be suffering from a variety of serious conditions, frequently are also prescribed additional drugs and thus are burdened with managing a complicated pharmaceutical regimen. Therefore, it may be desirable to combine multiple drugs in a combination dosage form for ease of administration and improved therapeutic compliance. In particular, use of a combination of a peripheral opioid antagonist, such as axelopran, and an opioid agonist may address concerns of OIC before they develop.

Depending on the clinical need, opioid analgesics can be administered through oral, transdermal and parenteral routes for either chronic or acute use, of which oral administration is commonly preferred. While immediate release opioids provide efficacious pain management, especially for acute and break-through pain, controlled or extended release opioids have demonstrated significant clinical value. However, the prophylactic effect of a peripheral opioid antagonist is typically achieved by immediate release of the antagonist agent. It would be desirable to provide a dosage form that combines a peripheral opioid antagonist in an immediate release form with an opioid analgesic agent that may be in an immediate release or in a modified (controlled or extended or sustained) release dosage form.

However, there are several technical problems that can arise when combining a peripheral opioid antagonist with an opioid analgesic agent. First, the peripheral opioid antagonist must be sufficiently stable during storage of the dosage form. For example, axelopran is known to degrade due to oxidation in its amorphous form. Additionally, the peripheral opioid antagonist should not significantly affect the release profile or other properties of the opioid analgesic agent.

SUMMARY OF THE INVENTION

The present invention provides a combination dosage form comprising a peripheral mu opioid receptor antagonist, such as axelopran, in an immediate release form and an opioid analgesic agent in a solid dosage form presented either in an immediate release or a modified release form. In one aspect, the present invention relates to a drug overcoat formulation comprising axelopran in an immediate release formulation and to a method of preparing such a drug over-coated opioid combination product.

Axelopran has been shown to be stable as the crystalline sulfate salt while amorphous axelopran is known to be insufficiently stable for use in a drug product. The present invention is made possible by the discovery of the key requirements for the conversion of amorphous axelopran to crystalline axelopran during or after any drug product preparation process that may initially form amorphous axelopran. Specifically, by the judicious choice of excipients and relative ratio of excipients to axelopran and, optionally, further by control of process conditions, a solid composition comprising axelopran sulfate in crystalline form with desirable physical properties may be prepared.

In one aspect, therefore, the invention provides a solid composition comprising axelopran sulfate and a film forming polymer. In one aspect, the film forming polymer is polyvinyl alcohol. In one aspect, the solid composition further comprises a plasticizer and optionally an antioxidant. In one aspect, the plasticizer is polyethylene glycol 3350 and the antioxidant is ascorbic acid. In one aspect, the solid composition comprises (a) between about 50% and about 95% by weight axelopran sulfate, (b) between about 5% and about 50% by weight polyvinyl alcohol, (c) between about 0% and about 45% polyethylene glycol 3350, and (d) between about 0% and about 10% ascorbic acid.

In one aspect, the solid composition of the invention comprises axelopran sulfate in crystalline form. In one aspect the solid composition comprising crystalline axelopran sulfate is stable upon storage at accelerated conditions for about 3 months. The solid composition may form a solid bead or may serve as a film or coating on an inert solid tablet or on a solid dosage form.

The ability to provide formulations that can controllably convert amorphous axelopran to a stable crystalline form has broad utility for the development of stable combination products. Commercial opioid products as well as those in development have resulted from significant research effort to provide modified release, as well as abuse-deterrent, properties. The present approach allows axelopran to be combined with the broad range of opioid products currently on the market or in development without significantly affecting the release profile or abuse-deterrent properties of the opioid analgesic agent.

In one aspect, the combination dosage form comprises axelopran or a pharmaceutically acceptable salt thereof as an active coating layer, equivalently termed a drug overcoat layer, on an opioid analgesic dosage form. In one aspect, the active coating layer comprises the solid composition of the invention. Thus, in one aspect, the active coating layer comprises axelopran sulfate and a film forming polymer. In another aspect, the active coating layer comprises axelopran sulfate, a film forming polymer, a plasticizer, and optionally an antioxidant. In a further aspect, the active coating layer comprises axelopran sulfate in a crystalline form. Optionally, the combination dosage form further comprises a subcoat layer between the active coating layer and the opioid dosage form.

In one aspect, the dosage form of the invention provides the benefit of a combination product that enables immediate release of a peripheral mu opioid receptor antagonist without affecting the drug release characteristics of an opioid analgesic agent from a modified (controlled or extended or sustained) release dosage form and further without affecting pharmacokinetic characteristics of each drug component.

Axelopran has been shown to be effective at ameliorating the symptoms of opioid-induced constipation at low dosages. In one aspect, the invention provides a combination dosage form comprising between about 2 mg and about 30 mg of axelopran in an immediate release formulation and an opioid analgesic agent in a modified release form. In one aspect, the opioid analgesic dosage form comprises oxycodone hydrochloride or oxymorphone hydrochloride.

In one aspect, the invention provides a method of treating pain in a mammal, the method comprising administering to the mammal a combination dosage form comprising a peripheral mu opioid receptor antagonist overcoated on an opioid analgesic agent. In one aspect the peripheral mu opioid receptor antagonist in the combination dosage form is axelopran or a pharmaceutically acceptable salt thereof. In another aspect, the peripheral mu opioid receptor antagonist in the combination dosage form is axelopran sulfate.

In one aspect, the invention provides a method of ameliorating a gastrointestinal side effect of opioid analgesic therapy, the method comprising administering the combination dosage form of axelopran or a pharmaceutically acceptable salt thereof and an opioid analgesic agent.

In a further aspect, the invention provides a method of forming the combination dosage form of the invention, the method comprising providing an opioid analgesic agent in a solid dosage form and coating the solid dosage form with a coating layer comprising axelopran or a pharmaceutically acceptable salt thereof.

DETAILED DESCRIPTION OF THE INVENTION

Definitions

Figure 1A:
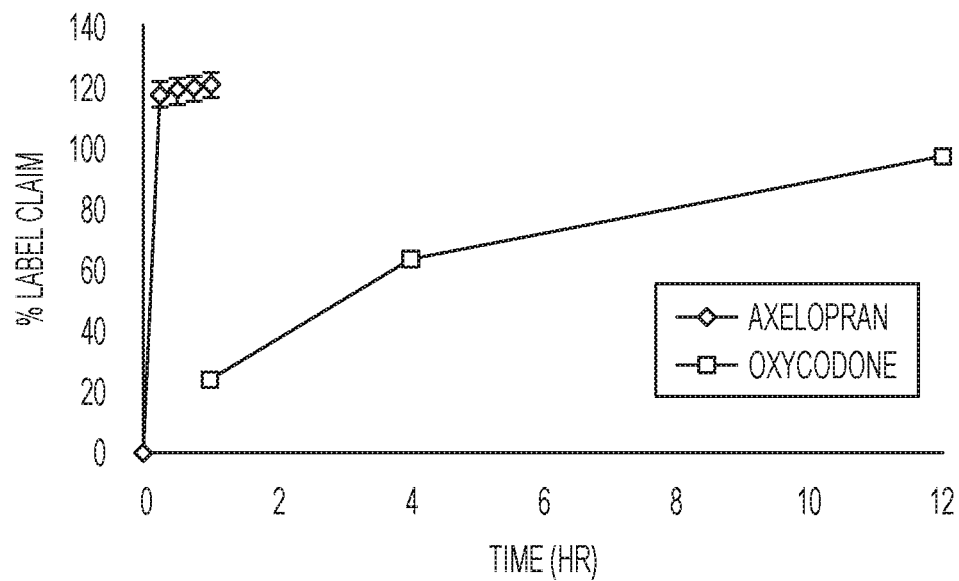
FIG. 1A and FIG. 1B show the percentage of drug (axelopran and oxycodone hydrochloride) dissolved as a function of time of a combination dosage form of axelopran (10 mg label claim) and oxycodone hydrochloride controlled-release tablet (20 mg label claim) for axelopran drug overcoat Formulation A and axelopran drug overcoat Formulation B, respectively.

As used herein, the term 'solid dosage form' refers to a pharmaceutical formulation in solid form for oral administration to a patient. The term comprises pills, tablets, beads, beadlets, microparticulates, and capsules. In particular, the term bead as used herein encompasses beadlets, microparticulates, and the like.

As used herein, the term 'modified release' form refers to a formulation of a drug product that alters the timing and/or rate of release of the active drug substance. The term 'modified release' form encompasses forms that are variously described as controlled-release, sustained-release, extended-release, and long-acting.

As used herein, the term 'immediate release' form refers to a formulation designed to release the active drug immediately upon oral administration. In immediate release formulations, no attempt has been made to modify the drug release rate.

In accordance with the present invention, a combination dosage form is provided which includes a peripheral mu opioid receptor antagonist, such as axelopran or a pharmaceutically acceptable salt thereof and an opioid analgesic agent. The opioid analgesic agent may be present in a modified release pharmaceutical formulation designed to affect the rate of release of the agent after administration to a patient, as defined herein. The opioid analgesic dosage form may also include abuse-deterrent properties.

Suitable opioid analgesic agents for inclusion in the present invention include oxycodone, hydrocodone, morphine, oxymorphone, and hydromorphone. Numerous controlled release or extended release formulations of these agents are available as commercial products or in early or late-stage development. Examples of such agents include, but are not limited to:

oxycodone: OxyContin® (oxycodone hydrochloride controlled release, Purdue Pharma), Oxycodone DETERx™ (oxycodone, extended release, Collegium Pharma), Egalet-002 (oxycodone, extended release, Egalet Corporation), hydrocodone: Hysingla™ ER (hydrocodone bitartrate, extended release, Purdue Pharma), Zohydro™ ER (hydrocodone bitartrate, extended release, Zogenix, Inc.), Vantrela™ (hydrocodone bitartrate, extended release, Teva Pharmaceutical Industries, Ltd)

morphine: Egalet-001 (Egalet Corporation), ER morphine (Inspirion Delivery Technologies), MS Contin® (Purdue Pharma)

oxymorphone: Opana® ER (oxymorphone hydrochloride, extended release, Endo Pharmaceuticals), Col-172 (Collegium Pharma)

hydromorphone: Exalgo® (hydromorphone hydrochloride, extended release, Mallinckrodt Pharmaceuticals)

Additional examples include products which also incorporate a non-opioid analgesic agent, in particular acetaminophen. Examples of such combinations include, but are not limited to:

Xartemis™ XR (oxycodone hydrochloride and acetaminophen, extended release, Mallinckrodt Pharmaceuticals)

MNK-155 (hydrocodone bitartrate and acetaminophen, controlled release, Mallinckrodt Pharmaceuticals)

As described in U.S. Pat. No. 7,943,772, axelopran sulfate forms a stable crystalline form while amorphous axelopran is not sufficiently stable for use in a drug product. As described therein, the crystalline form is characterized by a powder X-ray powder diffraction (PXRD) pattern having two or more diffraction peaks at 2θ values selected from 6.58±0.20, 7.52±0.20, 9.35±0.20, 14.69±0.20, 16.01±0.20, 17.45±0.20, 17.99±0.20, 18.62±0.20, 19.76±0.20, 21.11±0.20, 22.07±0.20, 23.18±0.20, 23.74±0.20, 24.56±0.20, 25.63±0.20, 26.45±0.20, 27.86±0.20, 28.31±0.20, 29.54±0.20, 30.59±0.20, 31.58±0.20, 33.89±0.20, and 36.02±0.20. In particular, stability of the axelopran sulfate crystalline form at accelerated conditions has been demonstrated. Thus, it is desirable for any drug product to comprise axelopran in a crystalline form.

The provision of stable combination dosage forms including axelopran is made possible by the discovery by the present inventors of the key requirements for the conversion of amorphous axelopran to crystalline axelopran during or after any process that may initially form amorphous axelopran. The choice of excipients in the coating solution was found to be one factor. As shown in Example 10 below, conventional coating polymers do not lead to films that are sufficiently stable when tested at accelerated conditions. The example also shows that the ratio of axelopran to excipients is another critical factor.

Figure 8:
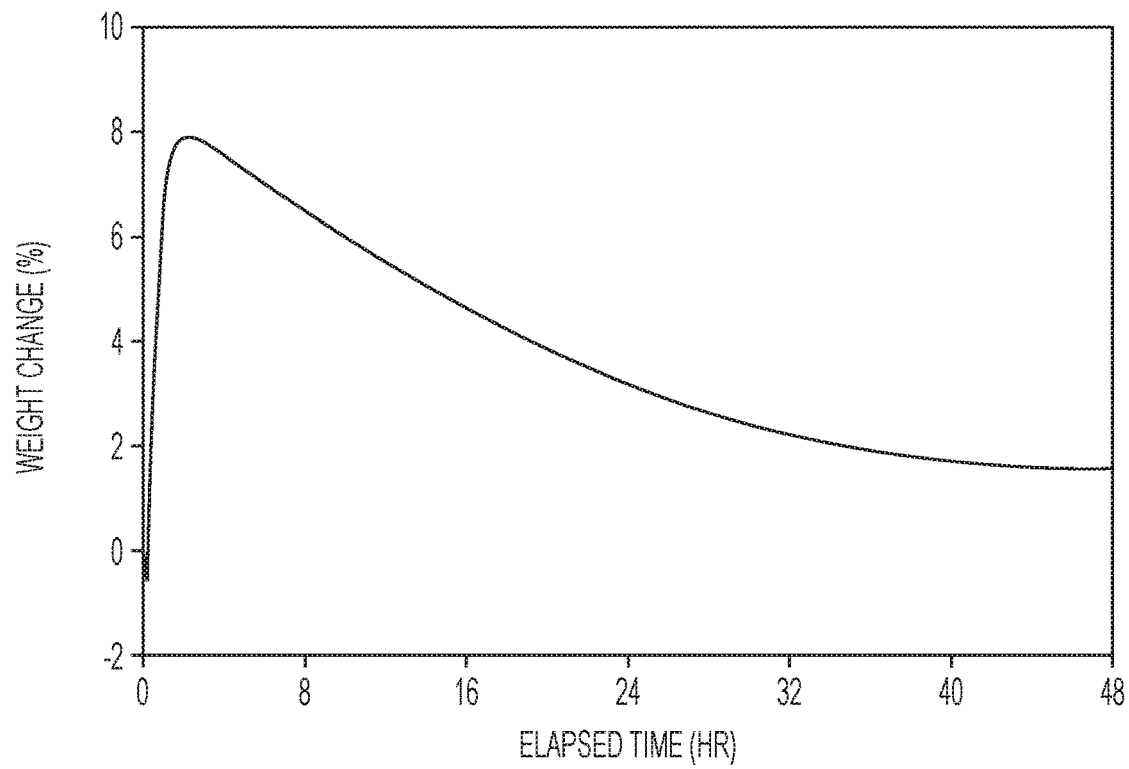
FIG. 8 shows the weight change of a spray coated film of axelopran sulfate and polyvinyl alcohol in a 4:1 wt/wt ratio subjected to 70% relative humidity at 25° C.

The present inventors have further demonstrated that high moisture content promotes crystallization as demonstrated in Example 11 and FIG. 8. A spray coated film of axelopran sulfate and polyvinyl alcohol in a 4:1 wt/wt ratio was subjected to 70% relative humidity for 48 hours at 25° C. The weight gain over the first two hours may be attributed to absorption of moisture by amorphous axelopran sulfate. The weight loss over the subsequent time period may be attributed to the crystallization of axelopran sulfate which releases the moisture absorbed by the amorphous form.

Oxidation has been identified as the main degradation pathway of amorphous axelopran. Therefore, in any process of preparing a layer containing crystalline axelopran from a solution in which the compound is amorphous, it is useful to control oxidation before crystallization takes place. While high moisture content was found to promote crystallization, at the same time, high moisture content promotes oxidation. One viable option, then, is to use an inert gas, such as nitrogen or argon, as an atomizing gas during a spray coating process to reduce or eliminate oxidation. Another option is to use an antioxidant in the formulation to control oxidation during spray coating.

Based on these discoveries, a solid composition that promotes crystallization of axelopran comprises axelopran sulfate and a film forming polymer. In another aspect, the solid composition comprises axelopran sulfate, a plasticizer, and optionally an antioxidant.

The solid composition may be prepared from an aqueous solution or a combination of water with a lower alcohol, for example, up to about 40% methanol or ethanol in water, but is preferably prepared from an aqueous-based solution. Examples of film forming polymers known in the art include, but are not limited to, polyvinyl alcohol, hydroxypropylmethyl cellulose, ethyl cellulose, hydroxypropyl cellulose, hydroxyethyl cellulose, copovidone, and combinations thereof. However, as exemplified below, it has been determined that not all film forming polymers are equally compatible with promoting axelopran crystallization and/or chemical stability. In a particular aspect, the film forming polymer is polyvinyl alcohol. Hydrophilic plasticizers known in the art include, but are not limited to, polyethylene glycols, glycerin, polyethylene glycol monomethyl ether, propylene glycol, triacetin, and sorbitol sorbitan solution. It has further been determined, that the choice of plasticizer is also important. Polyethylene glycol 3350 is particularly useful in the present formulation. Polyethylene glycol is an ethylene glycol polymer having an average molecular number of 3350. Antioxidants include, but are not limited to, ascorbic acid, propyl gallate, sodium sulfite, sodium metabisulfite, sodium bisulfite, thioglycerol, thioglycollic acid, butylated hydroxytoluene, butylated hydroxyanisole, and combinations thereof. A preferred antioxidant is ascorbic acid.

In the solid composition that promotes crystallization, axelopran sulfate is present in an amount ranging from about 50% to about 95% by weight, including from about 50% to about 85% by weight, and from about 50% to about 70% by weight. The film forming polymer, such as polyvinyl alcohol, is present in an amount between about 5% and about 50% by weight, including between about 10% and about 50% by weight, between about 10% and about 35% by weight, and between about 12% and about 25% by weight. The plasticizer, such as polyethylene glycol 3350, is present in an amount between about 0% and about 45% by weight, including between about 5% and about 30% by weight, and between about 12% and about 25% by weight. The optional antioxidant, such as ascorbic acid, is present in an amount between about 0% and about 10% by weight, including between about 0.5% and about 10% by weight, and between about 2% and about 6% by weight.

In one aspect, therefore, the invention provides a solid composition comprising:
(a) between about 50% and about 95% by weight axelopran sulfate,
(b) between about 5% and about 50% by weight polyvinyl alcohol,
(c) between about 0% and about 45% polyethylene glycol 3350, and
(d) between about 0% and about 10% ascorbic acid.

In another aspect, the invention provides a solid composition comprising:
(a) between about 50% and about 70% by weight axelopran sulfate,
(b) between about 10% and about 50% by weight polyvinyl alcohol,
(c) between about 5% and about 30% polyethylene glycol 3350, and
(d) between about 0.5% and about 10% ascorbic acid.

In yet another aspect, the solid composition comprises:
(a) between about 50% and about 70% by weight axelopran sulfate,
(b) between about 12% and about 25% by weight polyvinyl alcohol,
(c) between about 12% and about 25% polyethylene glycol 3350, and
(d) between about 2% and about 6% ascorbic acid.

As described above, the solid composition of the invention may be prepared from an aqueous solution or suspension, in particular a solution or suspension comprising axelopran sulfate, polyvinyl alcohol, optionally polyethylene glycol 3350 and optionally ascorbic acid. Typically, the solid composition is prepared from an aqueous solution. In the aqueous solution, axelopran, polyvinyl alcohol, optional polyethylene glycol 3350 and optional ascorbic acid are typically present in the same ratio as in the solid composition. The components of the solid composition, i.e. the non-aqueous components of the solution, collectively termed the 'solid content', may comprise between about 1% and about 50%, typically between about 5% and about 15%, for example, about 10%, of the aqueous solution, the remainder typically being purified water.

In another aspect, therefore, the invention provides an aqueous solution comprising between about 5% and about 15% solid content, wherein the solid content comprises axelopran sulfate, polyvinyl alcohol, optional polyethylene glycol 3350, and optional ascorbic acid in the ratios of the solid composition described above.

The solid composition may constitute one layer, i.e. the active coating layer, of a combination dosage form, or may form a coating on an inert solid tablet to provide axelopran as a monotherapy. Alternatively the solid composition may be prepared as a solid beadlet which, for example, may be combined with beadlets of a different agent in a combination dosage form.

In one aspect, the invention provides a combination dosage form comprising the solid composition of the invention as an active coating layer, equivalently termed a drug overcoat layer, on an opioid analgesic dosage form. In one aspect, the combination dosage form comprises crystalline axelopran sulfate. In one aspect, the drug overcoat layer comprising crystalline axelopran sulfate further comprises a film forming polymer and a plasticizer. The active coating layer comprising axelopran is designed to release drug in an immediate release pattern.

In another aspect, the invention provides a combination dosage form comprising an opioid analgesic solid dosage form and a drug overcoat layer comprising:
(a) between about 50% and about 70% by weight axelopran sulfate,
(b) between about 10% and about 50% by weight polyvinyl alcohol,
(c) between about 5% and about 30% polyethylene glycol 3350, and
(d) between about 0.5% and about 10% ascorbic acid.

In yet another aspect, the drug overcoat layer comprises:
(a) between about 50% and about 70% by weight axelopran sulfate,
(b) between about 12% and about 25% by weight polyvinyl alcohol,
(c) between about 12% and about 25% polyethylene glycol 3350, and
(d) between about 2% and about 6% ascorbic acid.

As described in the examples below, a particularly useful active drug coating layer comprises about 68% axelopran sulfate by weight, about 14% polyvinyl alcohol by weight, about 14% polyethylene glycol 3350 by weight, and about 4% ascorbic acid by weight, which corresponds to a weight ratio of axelopran free base equivalent:polyvinyl alcohol:polyethylene glycol 3350: ascorbic acid of 12:3:3:1.

Optionally, the combination dosage form further comprises a subcoat layer between the active coating layer and the opioid dosage form. It is convenient to employ the same film forming polymer and plasticizer in the subcoat layer as in the active coating. In a particular aspect, the combination dosage form of the present invention includes an optional subcoat layer comprising polyvinyl alcohol and polyethylene glycol 3350, for example in about a 1:2 ratio of polyvinyl alcohol to polyethylene glycol 3350.

The active coating may be prepared from an aqueous coating solution described above as the aqueous solution for the preparation of the present solid composition. A coating solution for applying the optional subcoat comprises between about 5% and about 15% subcoat components, i.e.

polyvinyl alcohol and polyethylene glycol 3350, with the remainder being purified water.

The present combination dosage form may be prepared by applying the aqueous coating solution described herein onto an optionally subcoated opioid tablet, pill, bead, beadlet, or capsule. The process of preparing the active coating layer and the optional subcoat layer may utilize a pan coater or fluid bed or wurster coating column. For example, as described in the appended examples, a pan coater may be used to spray coat a subcoat coating solution and subsequently the aqueous active layer coating solution onto opioid tablets. The process is typically performed at an exhaust temperature of about 40° C. Spray coating onto beads with a characteristic diameter of about 500 μm using a fluid bed has also been demonstrated.

In one aspect, therefore, the invention provides a method of preparing a combination dosage form, the method comprising (a) providing an opioid analgesic agent in a solid dosage form, and (b) coating the solid dosage form with a drug overcoat layer comprising axelopran sulfate and polyvinyl alcohol.

In a further aspect, a method of preparing a combination dosage form comprises: (a) providing an opioid analgesic agent in a solid dosage form, and (b) applying an aqueous coating solution comprising axelopran sulfate, polyvinyl alcohol, polyethylene glycol 3350, and optionally ascorbic acid. In yet another aspect, the method further comprises applying an aqueous subcoat coating solution comprising polyvinyl alcohol and polyethylene glycol 3350 onto the opioid solid dosage form before applying the active layer coating solution.

It has been discovered that subjecting a layer comprising axelopran sulfate in an amorphous form or in a form in which crystallization is incomplete to high relative humidity, for example between about 70% and about 86% relative humidity at a temperature between about 20° C. and about 45° C. results in conversion of amorphous axelopran sulfate to the crystalline form. In particular, it has been discovered that the ability to crystallize axelopran post-coating is enhanced by the specific formulation of the solid layer disclosed herein.

Figure 7:
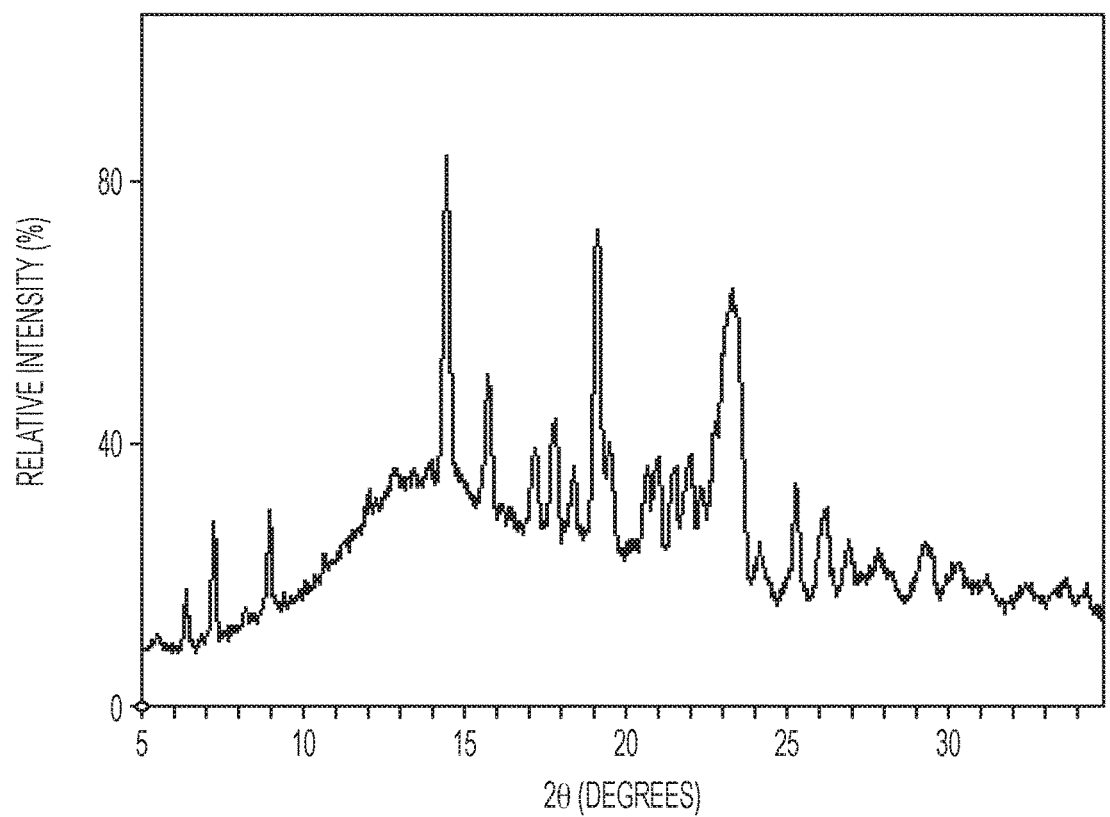
FIG. 7 shows a powder X-ray diffraction pattern of a combination dosage form of axelopran sulfate (10 mg label claim) and oxycodone hydrochloride controlled-release tablet (20 mg label claim) Formulation A obtained with a Bruker D8-Advance X-ray diffractometer using Cu-Kα radiation ($\lambda=1.54051$ Å) with output voltage of 45 kV and current of 40 mA.

The spray coating process parameters described below in Examples 2, 3, and 7 in which an aqueous solution is sprayed at 40° C. or 45° C. provide the conditions conducive to formation of crystalline axelopran sulfate, as demonstrated by the powder X-ray diffraction pattern of a combination dosage form prepared by the exemplified spray coating process shown in FIG. 7.

Furthermore, a combination dosage form prepared by a process such as that described in the examples has been shown to be stable upon storage. After three months at accelerated conditions of 40° C. and 75% relative humidity, no significant changes in axelopran content and impurity profile, as well as in the dissolution profile, were observed in a combination dosage of axelopran sulfate and oxycodone hydrochloride indicating good stability of the combination dosage form, which further may be taken as evidence of crystallinity.

Axelopran has been shown to be effective at ameliorating the symptoms of opioid-induced constipation at low dosages. By suitably adjusting the processing conditions, a combination dosage form containing between about 2 mg and about 30 mg axelopran per unit dosage may be prepared with good content uniformity. For example, the inventors have demonstrated a combination dosage form of about 10 mg axelopran coated onto 20 mg oxycodone hydrochloride controlled release tablets and onto 10 mg oxymorphone hydrochloride extended release tablets with a relative standard deviation of axelopran content of less than about 5%.

Figure 1B:
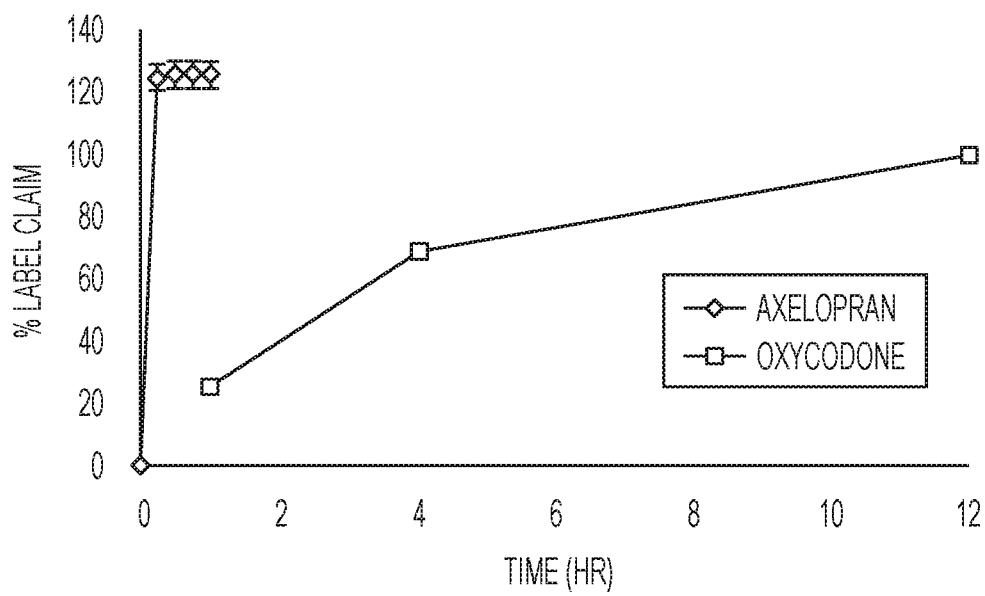
Figure 2A:
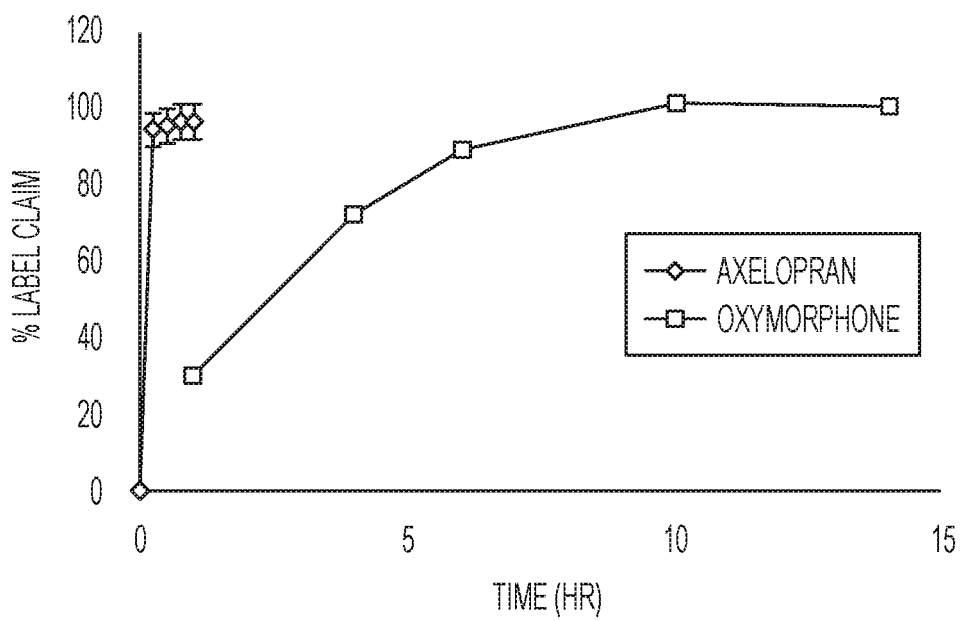
FIG. 2A and FIG. 2B show the percentage of drug (axelopran and oxymorphone hydrochloride) dissolved as a function of time of a combination dosage form of axelopran (10 mg label claim) and oxymorphone hydrochloride extended release tablet (10 mg label claim) for axelopran drug overcoat Formulation A and axelopran drug overcoat Formulation B, respectively.
Figure 2B:
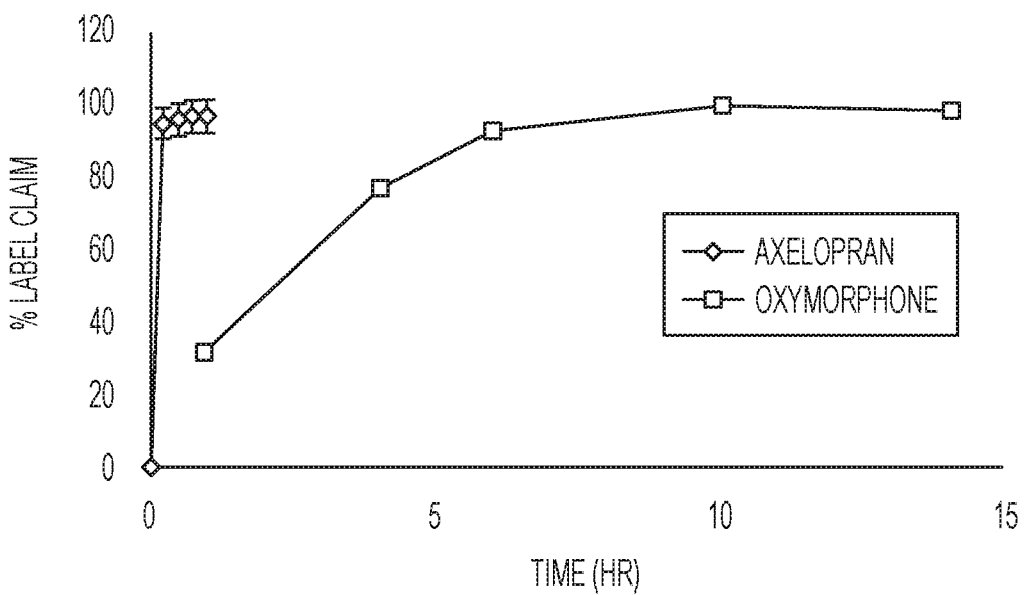

The present combination dosage form comprising an axelopran active coating and a modified release opioid exhibits immediate release of axelopran and extended release of the opioid. For example, the in vitro drug dissolution profile of an approximate 10 mg coating of axelopran overcoat on a controlled release oxycodone hydrochloride tablet (FIG. 1A and FIG. 1B) shows essentially all of the axelopran was released in the first quarter hour while the oxycodone was released gradually over 12 hours. Furthermore, the in vitro drug dissolution profile of the 10 mg axelopran coated oxycodone hydrochloride tablet that had been stored at 40° C. and 75% relative humidity was unchanged from the dissolution profile of time-zero tablets. Similarly, in vitro dissolution of axelopran coated oxymorphone hydrochloride extended release tablets demonstrates essentially all of the axelopran was released in the first quarter hour while the oxymorphone was released gradually over 12 hours (FIG. 2A and FIG. 2B).

In addition, the present combination dosage form has been shown in vivo to provide systemic exposure of the two components consistent with the exposures observed on co-administration of the two components in separate dosage forms. A pharmacokinetic study of axelopran coated oxycodone hydrochloride tablets and axelopran coated oxymorphone hydrochloride tablets in dogs is described in Example 8. Little difference is seen in the systemic exposure of oxycodone when administered as the combination dosage form with axelopran, as compared with the exposure from administration of axelopran and oxycodone in separate dosage forms, and with administration of oxycodone alone, in FIG. 3A. Systemic exposure of axelopran from the combination dosage form with oxycodone is shown to be consistent with exposure from administration in separate dosage forms and from administration of axelopran alone in FIG. 3B. Consistent exposures were also observed for the combination dosage form of axelopran and oxymorphone as illustrated in FIG. 4A and FIG. 4B.

Figure 5:
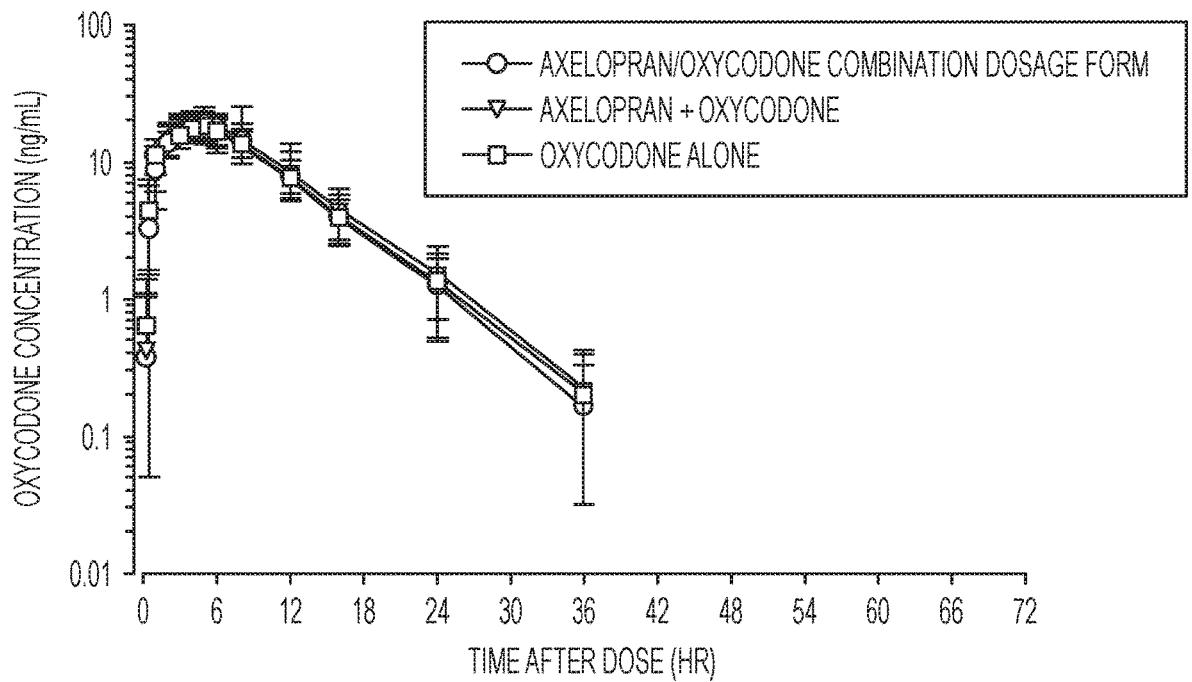
FIG. 5 shows the mean oxycodone plasma concentration±standard deviation (ng/mL) as a function of time from a single dose pharmacokinetic study in healthy human subjects administered the combination dosage form of axelopran and oxycodone hydrochloride, co-administered the two components as individual tablets and administered the components individually.

The present combination dosage form of axelopran and oxycodone was also studied in healthy human subjects. Taking co-administration of the individual tablets as the reference product, the combination dosage form of 10 mg axelopran and 20 mg oxycodone hydrochloride demonstrated total exposure of axelopran within 16% of the reference value and total exposure of oxycodone within 5% of the reference value in healthy human subjects. Furthermore, the oxycodone exposure satisfied the US FDA guidelines for bioequivalence as compared with the reference product. Also, the total exposure of oxycodone from the combination was equivalent to the exposure experienced when oxycodone was administered alone. As illustrated in FIG. 5, the combination dosage form of axelopran and oxycodone did not alter the systemic exposure of oxycodone.

Utility

The opioid therapeutic agents such as oxycodone, hydrocodone, morphine, and oxymorphone, are widely used for the treatment of pain including severe pain, chronic pain, and non-cancer pain such as musculoskeletal pain and post-operative pain. As the combination dosage form of axelopran and an opioid analgesic agent is expected to provide equivalent exposure of the opioid after oral administration, the present combination dosage form is expected to be useful for the treatment of pain.

In one aspect, therefore, the invention provides a method of treating pain in a mammal, particularly a human patient, the method comprising administering to the mammal a combination dosage form comprising axelopran and an opioid analgesic agent. In one aspect, the invention provides a method of treating pain comprising administering a combination dosage form comprising axelopran in an immediate release formulation and an opioid analgesic agent in a modified release formulation.

The mu opioid receptor antagonist axelopran has been shown to ameliorate the symptoms of opioid-induced constipation in patients on a stable opioid regimen, that is to reduce one of the distressing side effects of opioid therapy. As the combination dosage form of axelopran and an opioid analgesic is also expected to provide equivalent exposure of axelopran as compared with administration of axelopran separately, the present combination is expected to be useful for the amelioration of opioid-induced gastrointestinal side effects. In another aspect, therefore, the present invention provides a method of ameliorating a gastrointestinal side effect of opioid therapy in a mammal, in particular a human patient, the method comprising administering to the mammal a combination dosage form comprising axelopran and an opioid analgesic agent.

EXAMPLES

The following examples are offered to illustrate the invention, and are not to be construed in any way as limiting the scope of the invention.

For all of the following examples, axelopran sulfate was synthesized according to the process described in U.S. Pat. No. 7,943,772. A clinical tablet formulation of axelopran was used as the test article for the in vivo studies. Oxycodone was provided as commercially-obtained OxyContin® (oxycodone hydrochloride controlled release, 20 mg) tablets. According to the package insert, the tablets contain 20 mg oxycodone per tablet as the hydrochloride salt and the following inactive ingredients: butylated hydroxytoluene, hypromellose, polyethylene glycol 400, polyethylene oxide, magnesium stearate, titanium dioxide, polysorbate 80, and red iron oxide. Oxymorphone was provided as commercially-obtained Opana® ER (oxymorphone hydrochloride extended release, 10 mg) tablets. According to the package insert, the oxymorphone tablets contain 10 mg oxymorphone hydrochloride per tablet and the following inactive ingredients: hypromellose, polyethylene oxide, polyethylene glycol, α-tocopherol, citric acid, polyvinyl alcohol, titanium dioxide, macrogol, talc, and FD&C yellow No. 6.

Example 1: Spray Coating Process

A Thomas Compu-Lab 19 inch pan coater was used to prepare the combination dosage forms of Examples 2 and 3. Processing parameters optimized for coating performance and efficiency are summarized in Table 1.

TABLE 1

Processing Parameters

| | Set I | Set II |
|---|---|---|
| Exhaust Temp (° C.) | 40[a] | 40[a] |
| Solution Spray Rate (g/mL) | 15 | 13 |
| Atomizing Air Pressure (psi) | 35[b] | 35[b] |
| Pan Speed (rpm) | 15 | 15 |
| Air Flow Rate (scfm) | 170 | 170 |
| Inlet Temp (° C.) | 65 | 65 |
| Gun to Bed Distance (inches) | 7 | 7 |

[a]Range: 35-50
[b]Range: 25-45

Example 2: Preparation of Combination Dosage Form of Axelopran (10 mg) and Oxycodone Hydrochloride (20 mg)

Placebo cores were manufactured to match the OxyContin® tablets and were used as the main load of the substrate for the coating.

(a) Preparation of Subcoat

To prepare the coating solution, polyvinyl alcohol (40 g) was added to heated purified water USP. The mixture was stirred and heated to dissolution and then polyethylene glycol 3350 (80 g) was added and the mixture was stirred to dissolution. Purified water USP was added with stirring to provide a solution of approximately 10% solid content (i.e., non-aqueous content; the solid content is not in solid form).

A total of approximately 4 kg of placebo cores and a small number of OxyContin® tablets were spray coated with the subcoat solution according to the processing parameters of Table I Set I to achieve an approximate 3% weight gain of the sub-coat composition listed in Table 2.

TABLE 2

Sub-coat Formulation Composition

| | | Formulation Composition | |
|---|---|---|---|
| Component | | % wt | Unit Dose (mg/Tab) |
| Polyvinyl Alcohol, USP | | 33.3 | 1.56 |
| Polyethylene Glycol 3350, NF, EP | | 66.7 | 3.12 |

(b) Preparation of Active Coating Layer

Quantities of components to create active coating solutions for two formulations are listed in Table 3. To prepare each active coating solution, polyvinyl alcohol was added to heated purified water USP. The mixture was stirred and heated to dissolution and then polyethylene glycol was added, the mixture was stirred to dissolution, and ascorbic acid was added with stirring followed by axelopran sulfate. Purified water USP was added with stirring to provide a coating solution of approximately 10% solid content (e.g., non-aqueous content; the solid content is not in solid form).

TABLE 3

Axelopran Drug Active Coating Layer Formulation Compositions

| | Formulation A | | | Formulation B | | |
|---|---|---|---|---|---|---|
| | Part[a] | Unit Dose (mg/Tab) | Batch Quantity (g) | Part[a] | Unit Dose (mg/Tab) | Batch Quantity (g) |
| Axelopran sulfate | 12 | 12.27 | 314.6 | 12 | 12.27 | 314.6 |
| Ascorbic Acid, USP | 1 | 0.83 | 21.4 | 2 | 1.67 | 42.7 |
| Polyvinyl Alcohol, USP | 3 | 2.5 | 64.1 | 3 | 2.5 | 64.1 |
| Polyethylene Glycol 3350 | 3 | 2.5 | 64.1 | 6 | 5.0 | 128.2 |

[a]Axelopran free base equivalent

Upon completion of the sub-coating, the sub-coated placebo cores and opioid tablets were retained in the pan coater and further spray coated with the active coating solution according to the processing parameters of Table 1 Set I to achieve the target weight gain. Coated opioid tablets were separated from coated placebo cores by the difference in color upon completion of the coating.

Example 3: Preparation of Combination Dosage Form of Axelopran (10 mg) and Oxymorphone Hydrochloride (20 mg)

Placebo cores were manufactured to match the Opana® ER tablets and were used as the main load of the substrate for the coating.

(a) Preparation of Subcoat

A subcoat coating solution was prepared as in Example 2(a). A total of approximately 4 kg of placebo cores and a small number of Opana® ER tablets were spray coated according to the processing parameters of Table I Set II resulting in an approximate 3% weight gain of the sub-coat composition listed in Table 2.

(b) Preparation of Active Coating Layer

Coating solutions for the two formulations of Table 3 were prepared as described in Example 2(a). Upon completion of the sub-coating, the sub-coated placebo cores and opioid tablets were retained in the pan coater and further spray coated with the active coating solutions according to the processing parameters of Table 1 Set I to achieve the target weight gain. Coated opioid tablets were separated from coated placebo cores by the difference in color upon completion of the coating.

Example 4: Analysis of Drug Content Uniformity

The axelopran drug overcoated opioid tablets (n=10 tablets per formulation) were analyzed for drug content potency and uniformity by high-pressure liquid chromatography (HPLC) with UV detection. Results for the combination dosage forms prepared in Examples 2 and 3 are reported in Table 4.

TABLE 4

Axelopran Drug Content Potency and Uniformity

|  | Example 2 oxycodone | | Example 3 oxymorphone | |
| --- | --- | --- | --- | --- |
|  | Formulation A | Formulation B | Formulation A | Formulation B |
| Axelopran content (% Label claim)[a] | 118.5% | 125.7% | 92.6% | 94.1% |
| Axelopran uniformity (Relative standard deviation) | 3.14% | 3.26% | 5.76% | 4.94% |

[a]Label claim = 10 mg axelopran

Example 5: Drug Dissolution Profile

The axelopran coated opioid tablets of Examples 2 and 3 (n=6 tablets per formulation) were tested for drug dissolution rate of the individual components according to USP monograph 711 and in-house developed methodologies. Sample aliquots were collected at 13, 30, 45, 60, minutes, and at 4 and 12 hour dissolution time points and analyzed by reverse-phase HPLC with UV detection. The dissolution rate results for the individual components from the axelopran coated oxycodone tablets are shown in Table 5 and in FIGS. 1A and 1B, while the analogous dissolution rate results for axelopran coated oxymorphone tablets are shown in Table 6 and in FIGS. 2A and 2B. In all cases, essentially all of the axelopran is observed to have dissolved by the first time point of 0.25 hour while the controlled release opioid dissolved gradually over 12 hours.

TABLE 5

In vitro Dissolution of Axelopran/Oxycodone Combination Dosage Form

| | Time (hr) | % LC (Ave)[a] | % LC (% RSD)[b] |
| --- | --- | --- | --- |
| *Example 2 Formulation A* | | | |
| Axelopran | 0 | 0 | 0 |
| | 0.25 | 118 | 3.37 |
| | 0.50 | 119 | 3.52 |
| | 0.75 | 120 | 3.19 |
| | 1.00 | 121 | 3.25 |
| Oxycodone | 1 | 24 | 4.15 |
| | 4 | 64 | 3.89 |
| | 12 | 97 | 3.49 |
| *Example 2 Formulation B* | | | |
| Axelopran | 0 | 0 | 0 |
| | 0.25 | 124 | 3.24 |
| | 0.50 | 125 | 3.32 |
| | 0.75 | 125 | 3.31 |
| | 1.00 | 125 | 3.34 |
| Oxycodone | 1 | 25 | 2.13 |
| | 4 | 68 | 1.71 |
| | 12 | 98 | 2.18 |

[a]% Label claim with respect to axelopran 10 mg
[b]Relative Standard Deviation

TABLE 6

In vitro Dissolution of Axelopran/Oxymorphone Combination Dosage Form

| | Time (hr) | % LC (Ave)[a] | % LC (% RSD)[b] |
| --- | --- | --- | --- |
| *Example 3 Formulation A* | | | |
| Axelopran | 0 | 0 | 0 |
| | 0.25 | 94 | 4.63 |
| | 0.50 | 95 | 4.67 |
| | 0.75 | 96 | 4.62 |
| | 1.00 | 96 | 4.65 |
| Oxymorphone | 1 | 29 | 1.93 |
| | 4 | 72 | 2.09 |
| | 6 | 89 | 1.97 |
| | 10 | 101 | 1.57 |
| | 14 | 101 | 1.75 |
| *Example 3 Formulation B* | | | |
| Axelopran | 0 | 0 | 0 |
| | 0.25 | 94 | 4.63 |
| | 0.50 | 95 | 4.67 |
| | 0.75 | 96 | 4.62 |
| | 1.00 | 96 | 4.65 |
| Oxymorphone | 1 | 31 | 6.18 |
| | 4 | 76 | 5.52 |
| | 6 | 92 | 3.43 |
| | 10 | 99 | 1.25 |
| | 14 | 98 | 1.17 |

[a]% Label claim with respect to axelopran 10 mg
[b]Relative Standard Deviation

Example 6: Stability Study

Samples of an axelopran sulfate/oxycodone hydrochloride combination dosage form with the active coating layer formulation of Example 2 Formulation A stored at accelerated conditions of 40° C. and 75% relative humidity (RH) were analyzed by HPLC for axelopran content and impurity profile as shown in Table 7 and for dissolution rate as shown in Table 8.

TABLE 7

Axelopran Assay and Impurities (n = 3)

| RRT | T = 0 % a/a | T = 1 Month 40° C./75% RH % a/a | T = 3 Month 40° C./75% RH % a/a |
|---|---|---|---|
| 0.80 | 0.201 | 0.189 | 0.193 |
| 0.92 | 0.021 | 0.050 | 0.071 |
| 1.15 | 0.069 | 0.092 | 0.098 |
| 1.35 | 0.222 | 0.232 | 0.237 |
| 1.44 | 0.092 | 0.110 | 0.103 |
| | % LC | % LC | % LC |
| Axelopran | 96.18 | 93.018 | 91.187 |

TABLE 8

In vitro Dissolution of Axelopran/Oxycodone Combination Dosage Form (n = 6)

| | Time (hr) | T = 0 % LC (Ave)$^a$ | T = 0 % LC (% RSD)$^b$ | T = 1 Month 40° C./75% RH % LC (Ave)$^a$ | T = 1 Month 40° C./75% RH % LC (% RSD)$^b$ | T = 3 Month 40° C./75% RH % LC (Ave)$^a$ | T = 3 Month 40° C./75% RH % LC (% RSD)$^b$ |
|---|---|---|---|---|---|---|---|
| Axelopran | 0 | 0 | 0 | 0 | 0 | 0 | 0 |
| | 0.25 | 94.2 | 5.53 | 92.2 | 3.05 | 95.4 | 6.06 |
| | 0.50 | 95.3 | 5.23 | 93.0 | 2.95 | 96.9 | 6.13 |
| | 0.75 | 95.6 | 5.18 | 93.4 | 2.95 | 97.8 | 5.91 |
| | 1.00 | 95.9 | 5.10 | 93.8 | 2.93 | 98.3 | 5.83 |
| Oxycodone | 1 | 25.3 | 2.78 | 23.4 | 5.35 | 23.9 | 5.13 |
| | 4 | 67.9 | 3.15 | 67.0 | 2.79 | | |
| | 12 | 98.1 | 3.44 | 97.0 | 5.52 | 97.4 | 2.48 |

$^a$% Label claim with respect to axelopran 10 mg
$^b$Relative Standard Deviation

Example 7: Preparation of Axelopran Coated Beads

The feasibility of preparing a combination dosage form on a solid dosage form composed of beads was demonstrated by coating sugar spheres having a characteristic diameter of 500 μm.

The composition to prepare a nominal 10 mg axelopran coating per 450 mg of beads is listed in Table 9.

TABLE 9

Axelopran coated bead batch composition

| Ingredient | w/w % | Batch Quantity (g) |
|---|---|---|
| Subcoat | | |
| Sugar Spheres 30/35 | 87.24 | 174.50 |
| Polyvinyl alcohol, USP | 2.91 | 5.82 |
| Polyethylene glycol 3350 | 5.81 | 11.63 |
| Purified Water | — | 157.00 |
| Total | 95.96 | 192.00 |
| Axelopran Drug Overcoat | | |
| Subcoated sugar spheres (beads) | 95.96 | 192.00 |
| Axelopran Sulfate | 2.75 | 5.50 |
| Ascorbic acid | 0.18 | 0.36 |
| Polyvinyl alcohol, USP | 0.56 | 1.12 |
| Polyethylene glycol 3350 | 0.56 | 1.12 |
| Purified Water | — | 72.90 |
| Total | 100 | 200.020 |

Three coating runs were performed:

A. Batch quantity 200 g with subcoat

A subcoat coating solution and axelopran active coating layer solution were prepared according to the process described in Example 2. Sugar beads were loaded into the bowl of a Glatt mini fluid bed and warmed to about 45° C. The subcoat coating solution was sprayed onto the beads at a spray rate of 0.6 g/min until a 10% weight gain was achieved. Upon completion of the subcoating, the active coating layer solution was sprayed onto the subcoated sugar beads at a spray rate of 0.6 g/min. The product temperature was maintained at about 45° C. in the fluid bed with atomization air pressure of 0.8 to 1.0 bar. Upon completion of deposition of the active coating layer, the beads were dried at 45° C. for 10 min before discharging.

B. Batch quantity 200 g without subcoat

An active coating layer solution of composition equivalent to that described in Table 8 was sprayed directly onto sugar beads as described above.

C. Batch quantity 2 kg with subcoat

Two batches of axelopran coated beads denoted C-1 and C-2, were prepared from compositions with batch quantity 10 times the quantities listed in Table 8 using a Glatt GPCG-3 fluid bed. Typical processing parameters are listed in Table 10.

TABLE 10

Fluid Bed Processing Parameters (2 kg batch)

| Column Height (mm) | 35 |
|---|---|
| Inlet Temp (° C.) | 52 |
| Outlet Temp (° C.) | 45 |
| Product Temp (° C.) | 45 |
| Solution Spray Rate (g/min) | 4.0 |
| Atomizing Air Pressure (psi) | 30 |
| Outlet Air Control Flap (%) | 40 |

The resulting beads were tested for content uniformity and main degradant.

TABLE 11

Content uniformity and purity

| | Batch A | Batch B | Batch C-1 | Batch C-2 |
|---|---|---|---|---|
| Axelopran content (% Label claim)$^a$ | 97.7% | 92.0% | 95.0% | 95.0% |

TABLE 11-continued

Content uniformity and purity

|  | Batch A | Batch B | Batch C-1 | Batch C-2 |
|---|---|---|---|---|
| Axelopran uniformity (Relative standard deviation) | 0.30% | 0.26% | 0.76% | 1.27% |
| Main Degradant (% area/area) | 0.094 | 0.37 | Not determined | Not determined |

[a]Label claim based on 10 mg dose

Example 8: Pharmacokinetics and Relative Bioavailability in Dogs

A single dose, four period, cross over pharmacokinetic study in fasted beagle dogs (6 male dogs per group) was conducted to assess pharmacokinetic characteristics and relative bioavailability of axelopran and opioid (oxycodone or oxymorphone) following oral administration of the present combination dosage form, co-administration of the individual components, and the individual dosage form of each component.

The combination dosage form of Example 2 Formulation A (11.85 mg axelopran, 19.42 mg oxycodone per tablet) and individual tablets axelopran (10.21 mg), oxycodone (19.42 mg) were used for the axelopran/oxycodone study. The combination dosage form of Example 3 Formulation A (9.26 mg axelopran, 10.39 mg oxymorphone) and individual tablets axelopran (10.21 mg), oxymorphone (10.39 mg) were used for the axelopran/oxymorphone study. A washout period between each phase of at least 5 days was observed. The dogs received an intramuscular pentagastrin (6 μg/kg) pretreatment to reduce stomach pH.

Figure 3A:
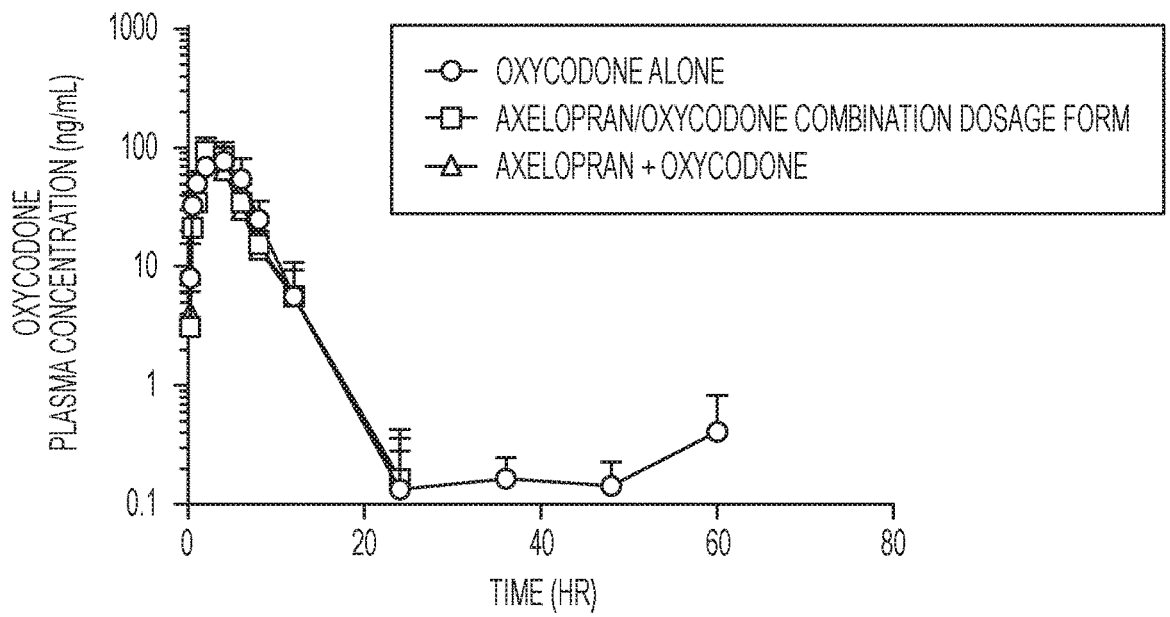
FIG. 3A and FIG. 3B show the mean plasma concentration±standard deviation (ng/mL) as a function of time of oxycodone hydrochloride and axelopran, respectively from a single dose pharmacokinetic study in beagle dogs administered the combination dosage form of axelopran and oxycodone hydrochloride, co-administered the two components as individual tablets, and administered the components individually.
Figure 3B:
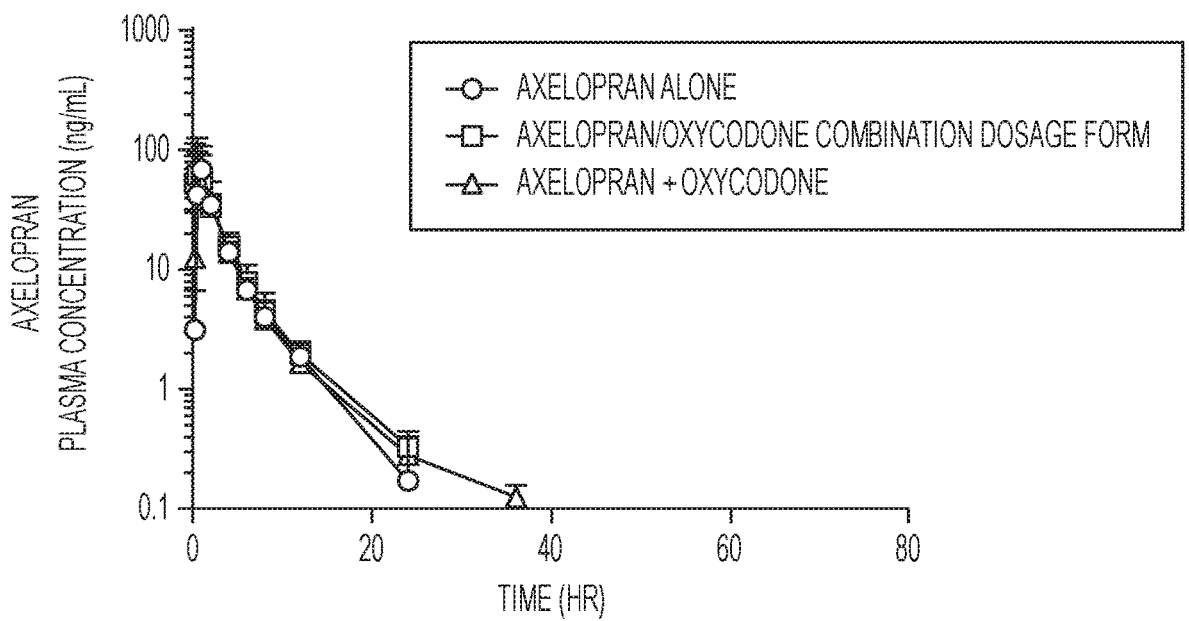
Figure 4A:
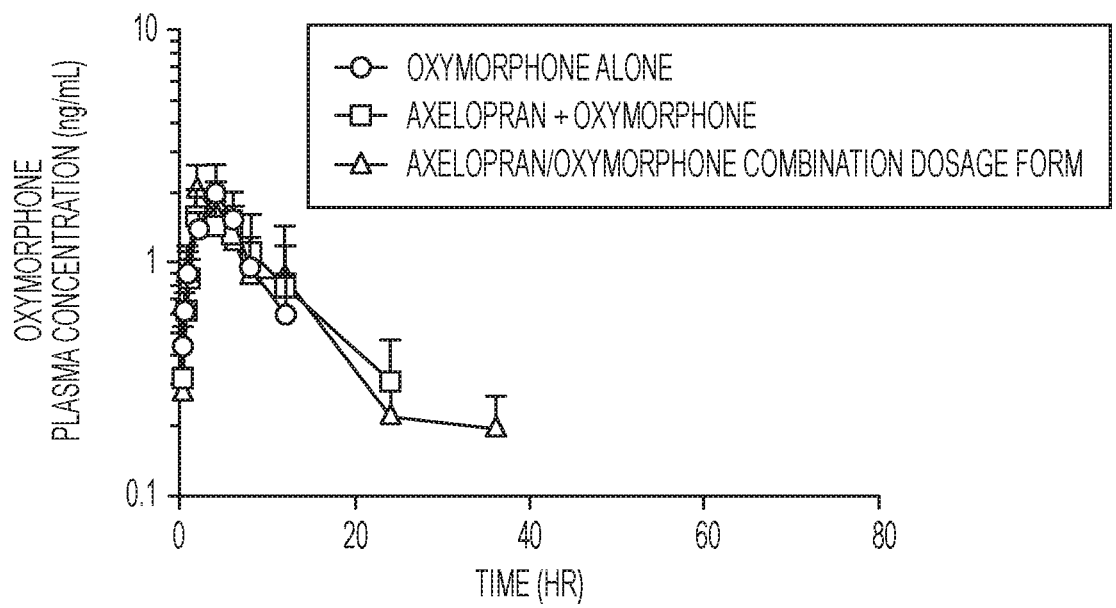
FIG. 4A and FIG. 4B show the mean plasma concentration±standard deviation (ng/mL) as a function of time of oxymorphone hydrochloride and axelopran, respectively, from a single dose pharmacokinetic study in beagle dogs administered the combination dosage form of axelopran and oxymorphone hydrochloride, co-administered the two components as individual tablets, and administered the components individually.
Figure 4B:
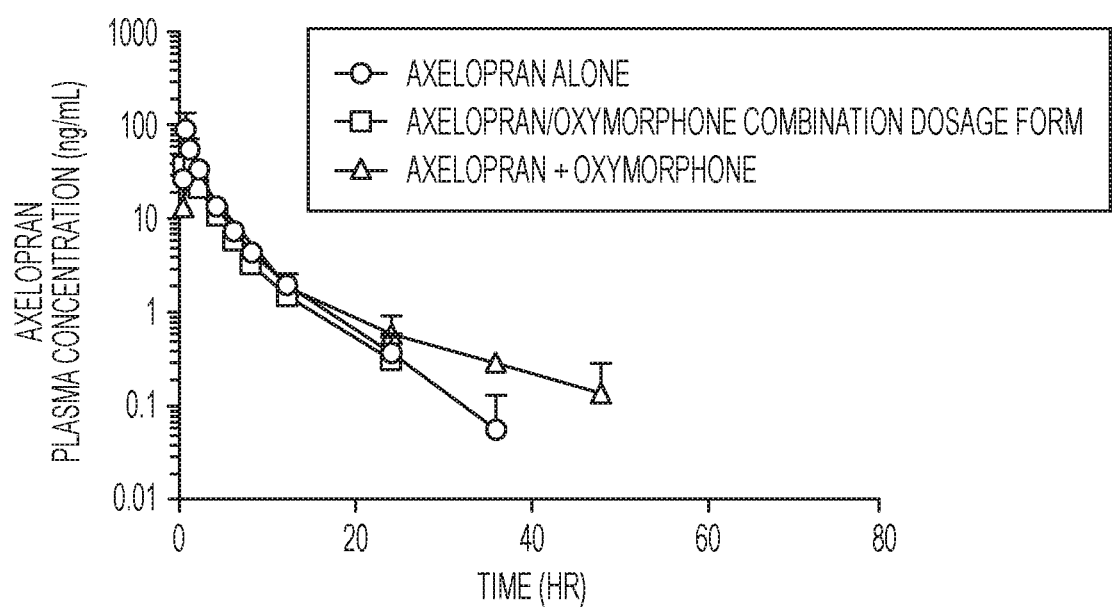

Plasma profiles of axelopran and opioid from the pharmacokinetic studies are shown in FIGS. 3A and 3B (oxycodone) and FIGS. 4A and 4B (oxymorphone), respectively.

Example 9: Pharmacokinetics and Relative Bioavailability in Healthy Human Subjects A randomized, single-dose, open-label, four treatment period four sequence cross over study of the relative bioavailability of axelopran and oxycodone after oral administration as the present combination dosage form, after co-administration of the individual components, and after administration of the individual dosage form of each component was studied in healthy human subjects. Naltrexone was administered 15 and 3 hours prior to and 9 and 21 hours after administration of each treatment to block the adverse effects of the opioid. A seven day washout period between each period was observed. The number of subjects who completed at least one period was 28 with 26 subjects completing all four study periods.

Overcoated combination tablets (9.66 mg axelopran, 19.42 mg oxycodone per tablet) were prepared according to the process of Example 2, axelopran layer in formulation A of Table 3. Individual tablets axelopran (10.21 mg), oxycodone (19.42 mg) were used for the study.

Figure 6:
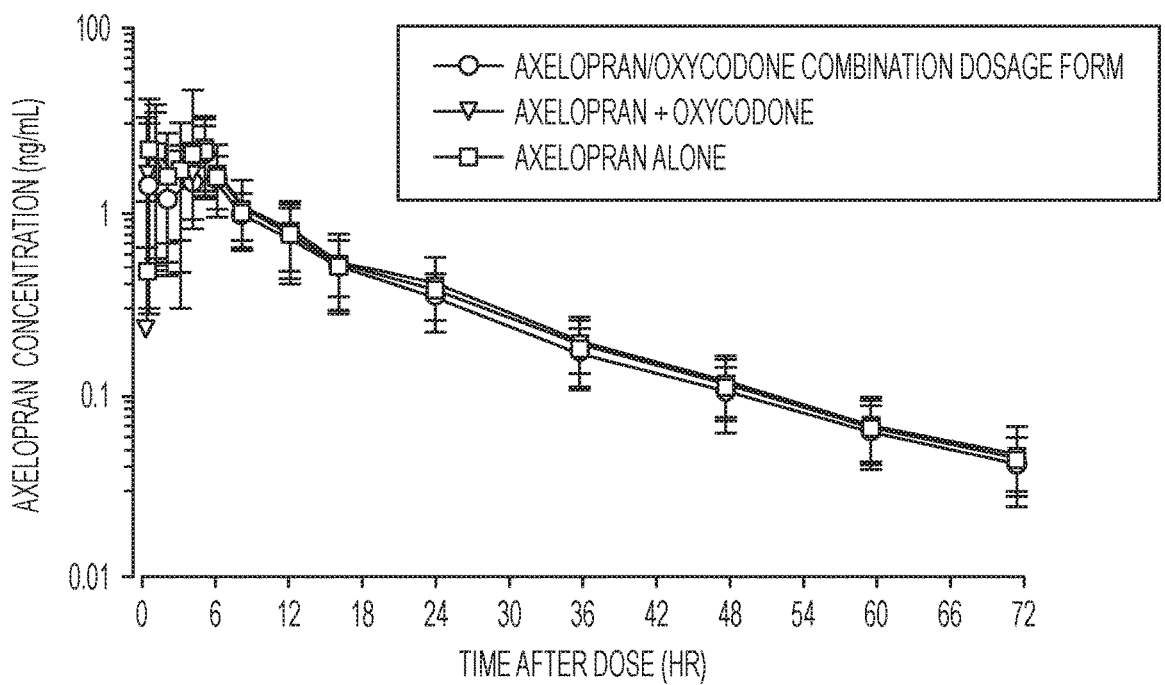
FIG. 6 shows the mean axelopran plasma concentration±standard deviation (ng/mL) as a function of time from a single dose pharmacokinetic study in healthy human subjects administered the present combination dosage form of axelopran and oxycodone hydrochloride, co-administered the two components as individual tablets and administered the components individually.

Pharmacokinetic (PK) parameters were determined by non-compartmental analysis using WinNonlin Version 6.2.1 (Pharsight, St. Lous, Mo.) The following PK parameters were reported:

$C_{max}$: maximum concentration in plasma $AUC_{0-last}$: area under the concentration-time curve from time of dosing to last measurable concentration $AUC_{0-\infty}$: area under the concentration-time curve extrapolated to infinity Relative bioavailability for oxycodone and axelopran for the combination dosage as compared with the co-administration of the individual components is given in Tables 12 and 14, respectively. The relative bioavailability of oxycodone for combination dosage compared with oxycodone alone is given in Table 13. Plasma exposures of oxycodone and axelopran are shown in FIG. 5 and FIG. 6, respectively.

The study demonstrated that the combination dosage form of axelopran and oxycodone provided clinically equivalent exposures to oxycodone and axelopran relative to co-administration of individual tablets. The oxycodone pharmacokinetic parameters $C_{max}$, $AUC_{0-last}$, and $AUC_{0-\infty}$ geometric mean ratios and the associated confidence intervals are within 80% to 125% of the reference product. The $C_{max}$, $AUC_{0-last}$, and $AUC_{0-\infty}$ geometric mean ratios for axelopran from the combination dosage with respect to co-administration of individual tablets are approximately 85%.

TABLE 12

Relative Bioavailability Of Oxycodone For Combination Dosage Form Compared With Co-Administration Of Individual Components

|  |  | $C_{max}$ (ng/mL) | $AUC_{0-last}$ (ng*hr/mL) | $AUC_{0-\infty}$ (ng*hr/mL) |
|---|---|---|---|---|
| Oxycodone + axelopran[c] Co-administration (Reference product) | Mean[a] | 19.6 | 218 | 220 |
| Oxycodone/ axelopran[d] Combination dosage form | Mean[a] | 20.0 | 209 | 212 |
| % Ref | | 101.9 | 96.0 | 96.0 |
| 90% CI[b] | | 95.2-109.2 | 92.7-99.5 | 92.6-99.5 |

[a]Geometric least squares mean from linear mixed effects analysis
[b]90% Confidence Interval of the ratio
[c]N = 27 for $C_{max}$ and $AUC_{0-last}$, N = 26 for $AUC_{0-\infty}$
[d]N = 27 for $C_{max}$, $AUC_{0-last}$, and $AUC_{0-\infty}$

TABLE 13

Relative Bioavailability Of Oxycodone For Combination Dosage Form Compared With Oxycodone Alone[a]

|  |  | $C_{max}$ (ng/mL) | $AUC_{0-last}$ (ng*hr/mL) | $AUC_{0-\infty}$ (ng*hr/mL) |
|---|---|---|---|---|
| Oxycodone tablet[c] (Reference product) | Mean[a] | 19.1 | 208 | 211 |
| Oxycodone/ axelopran[d] Combination dosage form | Mean[a] | 20.0 | 209 | 212 |
| % Ref | | 104.3 | 100.4 | 100.3 |
| 90% CI[b] | | 98.1-111.0 | 96.5-104.4 | 96.4-104.3 |

[a]Geometric least squares mean from linear mixed effects analysis
[b]90% Confidence Interval of the ratio
[c]N = 26 for $C_{max}$, $AUC_{0-last}$, and $AUC_{0-\infty}$
[d]N = 27 for $C_{max}$, $AUC_{0-last}$, and $AUC_{0-\infty}$

TABLE 14

Relative Bioavailability Of Axelopran For Combination Dosage Form Compared With Co-Administration of Individual Components[a]

| | | $C_{max}$ (ng/mL) | $AUC_{0-last}$ (ng*hr/mL) | $AUC_{0-\infty}$ (ng*hr/mL) |
|---|---|---|---|---|
| Oxycodone + axelopran[c] Co-administration (Reference product) | Mean[a] | 3.09 | 29.4 | 30.6 |
| Oxycodone/ axelopran[c] Combination dosage form | Mean[a] | 2.60 | 25.3 | 26.3 |
| | % Ref | 84.2 | 86.0 | 86.1 |
| | 90% CI[b] | 70.1-101.2 | 80.2-92.2 | 80.3-92.4 |

[a]Geometric least squares mean from linear mixed effects analysis
[b]90% Confidence Interval of the ratio
[c]N = 27 for $C_{max}$, $AUC_{0-last}$, and $AUC_{0-\infty}$ Example 10: Excipient Compatibility Study The compatibility of axelopran with four compositions of commercial coating materials was studied as a function of ratio of coating material to axelopran. Mixtures of axelopran sulfate and the materials of Table 15 were dried at 40° C. in weighing boats to form films. Chemical stability of the films stored at accelerated conditions of 40° C. and 88% relative humidity for 2 weeks were analyzed by HPLC.

TABLE 15

Coating materials

| Material No. | Material Name | Chemical Compositions |
|---|---|---|
| 1 | Opadry II Pink | Polyvinyl alcohol, titanium dioxide, PEG, Talc, yellow iron oxide, red iron oxide |
| 2 | Opadry II PVA Base Clear | Polyvinyl alcohol, Talc, PEG[a] 3350, Polysorbate 80 |
| 3 | HPMC/Triacetin/ Talc | HPMC[b], Triacetin, Talc |
| 4 | HPMC/PEG | HPMC[b], PEG 400 |

[a]polyethylene glycol
[b]hydroxypropylmethyl cellulose

TABLE 16

Axelopran Assay

| Material No. | Ratio of Coating Material to Axelopran[a] | T = 0 (% Area) | T = 2 Weeks (% Area) |
|---|---|---|---|
| Axelopran | N/A | 99.70 | N/A |
| 1 | 1/1 | 98.83 | 94.41 |
| | 3/1 | 97.97 | 86.48 |
| | 6/1 | 98.09 | 75.25 |
| 2 | 1/1 | 98.72 | 93.06 |
| | 3/1 | 97.54 | 77.00 |
| | 6/1 | 97.89 | 47.17 |
| 3 | 1/1 | 98.43 | 73.72 |
| | 3/1 | 97.72 | 55.11 |
| | 6/1 | 97.64 | 6.69 |
| 4 | 1/1 | 98.06 | 89.67 |
| | 3/1 | 96.29 | 14.62 |
| | 6/1 | 95.63 | 25.60 |

[a]Relative to axelopran free base equivalent

Example 11: Moisture Sorption Analysis of Axelopran Film

An aqueous solution of axelopran sulfate and polyvinyl alcohol in a 4:1 wt/wt ratio at 2.5% solid loading was spray coated onto a jacketed glass surface at 60° C. A small piece of film was placed in a moisture sorption analyzer (SGA-100, VTI Corp. Hialeah, Fla.). The humidity was set to about 0% relative humidity (RH) for 10 min and then raised to 70% RH for 48 hours. The temperature was set at 25° C. As shown in FIG. 8, the film increased in weight for the first two hours and began to lose weight after the initial gain. The weight gain over the first two hours may be attributed to absorption of moisture by amorphous axelopran sulfate. The weight loss over the subsequent time period may be attributed to the crystallization of axelopran sulfate which releases the moisture absorbed by the amorphous form. The net gain in film weight may be attributed to moisture sorption by the polyvinyl alcohol.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

We claim:

1. A method of treating pain in a mammal, the method comprising administering to the mammal a combination dosage form comprising:
   a solid dosage form comprising an opioid analgesic agent, and
   an immediate release portion comprising crystalline axelopran sulfate wherein the immediate release portion is a drug overcoat layer on the solid dosage form and wherein the drug overcoat layer comprises:
   (a) between about 50% and about 70% by weight axelopran sulfate,
   (b) between about 12% and about 25% by weight polyvinyl alcohol,
   (c) between about 12% and about 25% by weight polyethylene glycol 3350, and
   (d) between about 2% and about 6% by weight ascorbic acid.

2. A method of ameliorating a gastrointestinal side effect of opioid analgesic therapy in a mammal, the method comprising administering to the mammal a combination dosage form comprising:
   a solid dosage form comprising an opioid analgesic agent, and
   an immediate release portion comprising crystalline axelopran sulfate wherein the immediate release portion is a drug overcoat layer on the solid dosage form and wherein the drug overcoat layer comprises:
   (a) between about 50% and about 70% by weight axelopran sulfate,
   (b) between about 12% and about 25% by weight polyvinyl alcohol,
   (c) between about 12% and about 25% by weight polyethylene glycol 3350, and
   (d) between about 2% and about 6% by weight ascorbic acid.

3. The method of claim 2, wherein the gastrointestinal side effect of opioid analgesic therapy is opioid induced constipation.

4. The method of claim 2, wherein the gastrointestinal side effect of opioid analgesic therapy is delayed gastric emptying.

5. The method of claim 2, wherein the gastrointestinal side effect of opioid analgesic therapy is abdominal discomfort.

6. The method of claim 2, wherein the gastrointestinal side effect of opioid analgesic therapy is nausea.

7. The method of claim 2, wherein the opioid analgesic agent is in a modified release formulation.

8. The method of claim 2, wherein the solid dosage form comprising the opioid analgesic agent is a tablet or bead.

9. The method of claim 2, wherein the solid dosage form comprising the opioid analgesic agent is a tablet.

10. The method of claim 2, wherein the combination dosage form further comprises a subcoat layer between the drug overcoat layer and the solid dosage form comprising the opioid analgesic agent.

11. The method of claim 10, wherein the subcoat layer comprises polyvinyl alcohol and polyethylene glycol.

12. The method of claim 2, wherein the opioid analgesic agent is oxycodone or oxymorphone.

13. The method of claim 2, wherein the combination dosage form further comprises a subcoat layer wherein the subcoat layer comprises polyvinyl alcohol and polyethylene glycol and wherein the opioid analgesic agent is oxycodone or oxymorphone.

14. The method of claim 2, wherein the combination dosage form provides an in vitro rate of release of axelopran for less than one hour and an in vitro rate of release of the opioid analgesic agent for up to 12 hours.

* * * * *